(12) United States Patent
Fathallah et al.

(10) Patent No.: US 6,805,686 B1
(45) Date of Patent: Oct. 19, 2004

(54) AUTOINJECTOR WITH EXTENDABLE NEEDLE PROTECTOR SHROUD

(75) Inventors: Marwan A. Fathallah, Mundelein, IL (US); Richard W. Grabenkort, Barrington, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/430,710

(22) Filed: May 6, 2003

(51) Int. Cl.[7] ............................................... A61M 5/20
(52) U.S. Cl. ..................................... 604/135; 604/134
(58) Field of Search ................................ 604/135, 134, 604/131, 136, 137, 110, 193, 194, 195, 196, 192, 187, 221, 222, 223, 224, 225–234, 157

(56) References Cited

U.S. PATENT DOCUMENTS

| 4,425,120 A | 1/1984 | Sampson et al. |
| 4,573,976 A | 3/1986 | Sampson et al. |
| 4,850,994 A | 7/1989 | Zerbs et al. |
| 4,923,447 A | 5/1990 | Morgan |
| 5,201,708 A | 4/1993 | Martin |
| 5,242,240 A | 9/1993 | Gorham |
| 5,300,030 A | 4/1994 | Crossman et al. |
| 5,318,538 A | 6/1994 | Martin |
| 5,779,677 A | 7/1998 | Frezza |
| 6,099,503 A | 8/2000 | Stradella |
| 6,319,233 B1 | 11/2001 | Jansen et al. |
| 6,319,234 B1 | 11/2001 | Restelli et al. |
| 6,322,540 B1 | 11/2001 | Grabis et al. |
| 6,419,658 B1 | 7/2002 | Restelli et al. |

Primary Examiner—Manuel Mendez
(74) Attorney, Agent, or Firm—Beth A. Vrioni

(57) ABSTRACT

The invention provides a syringe and a method for using the same. The syringe includes a housing having a reservoir disposed therein and a plunger to be received by the reservoir, the plunger being moveable between a first plunger position and a second plunger position. The syringe also includes a plunger spring to urge the plunger toward the second plunger position and an actuator to deploy the plunger spring. The syringe also includes a needle proximate the distal end of the housing displaceable from a first needle position to a second needle position, and a shroud coupled with the housing. The shroud is moveable between a retracted position and an extended position, the shroud surrounding at least a portion of the needle when in the extended position. The syringe also includes an interlocking assembly, a shroud spring, and a locking assembly configured to inhibit movement of the shroud.

24 Claims, 12 Drawing Sheets

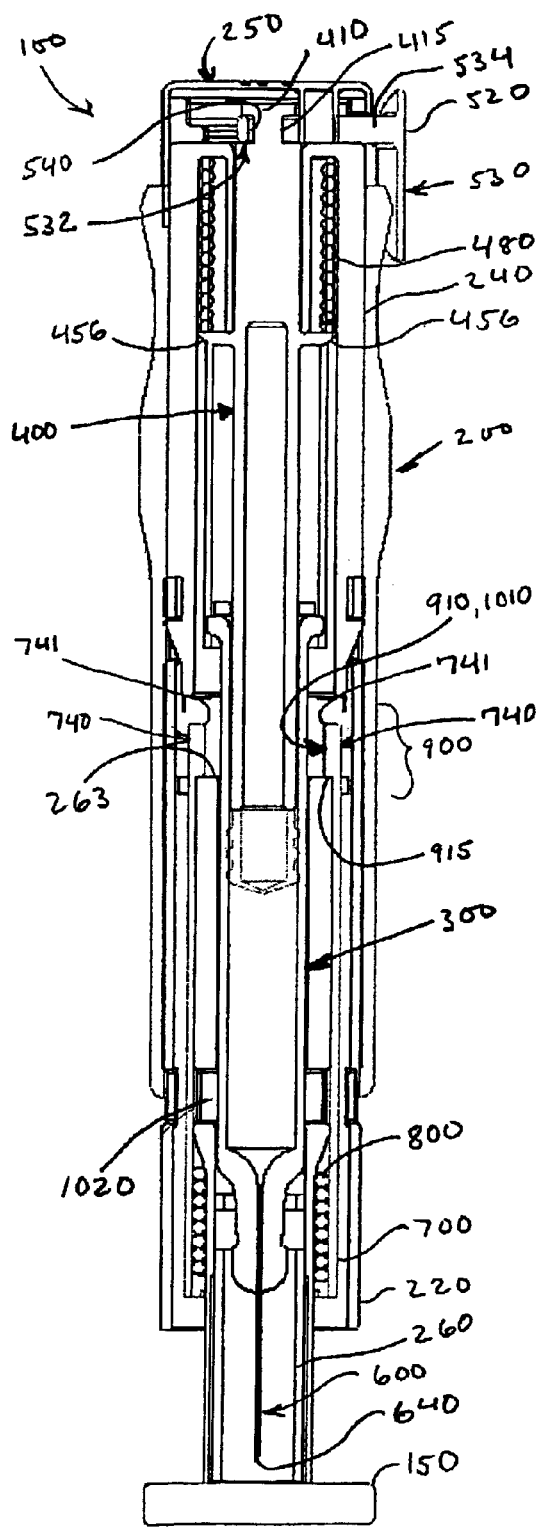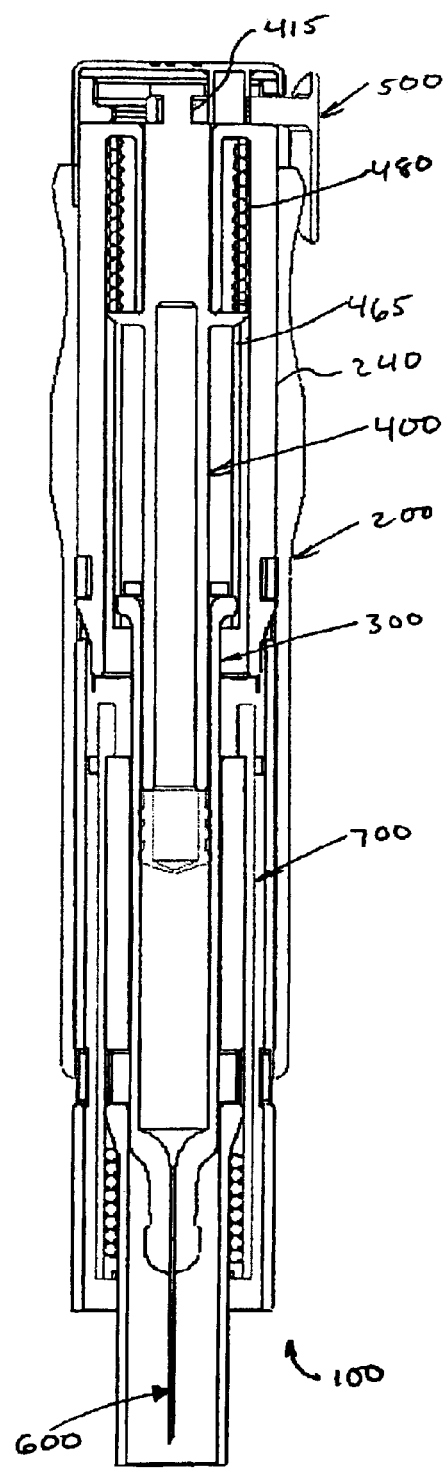
FIG. 4(a)
FIG. 4(b)

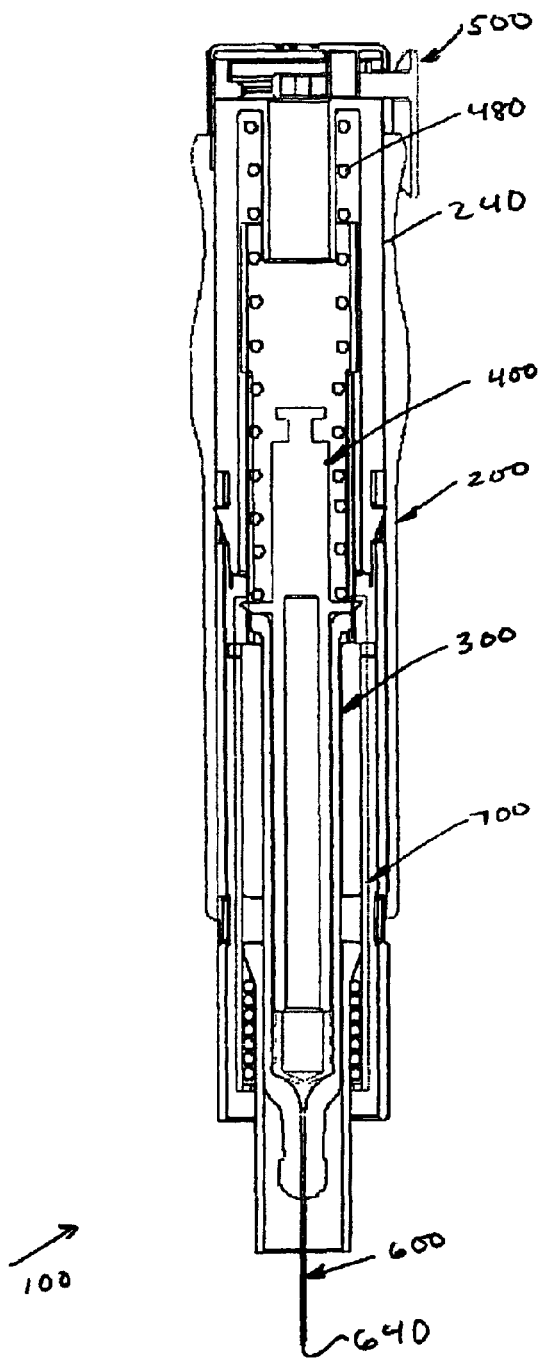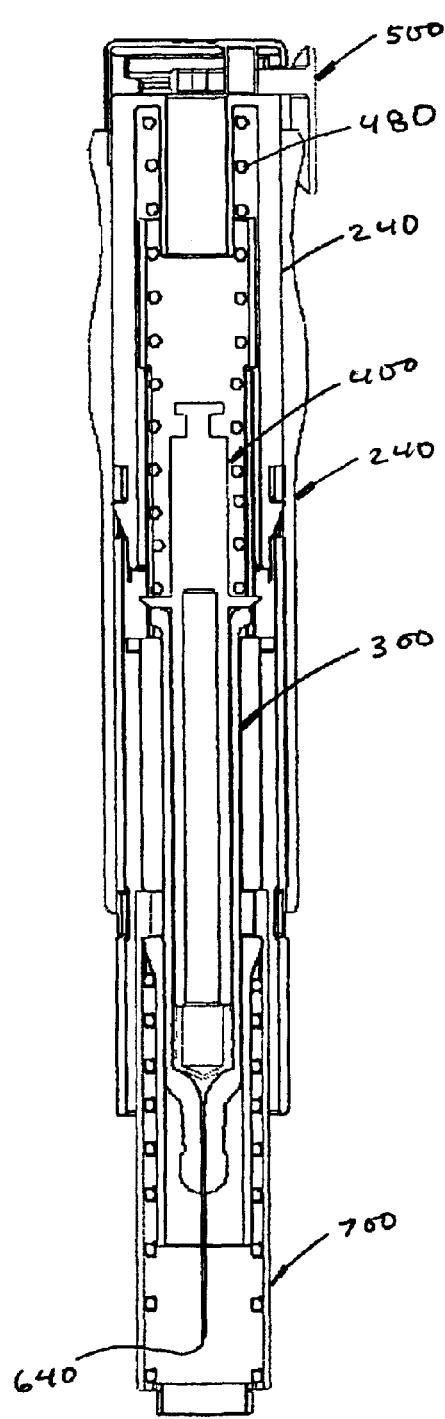
FIG. 4(c)
FIG. 4(d)

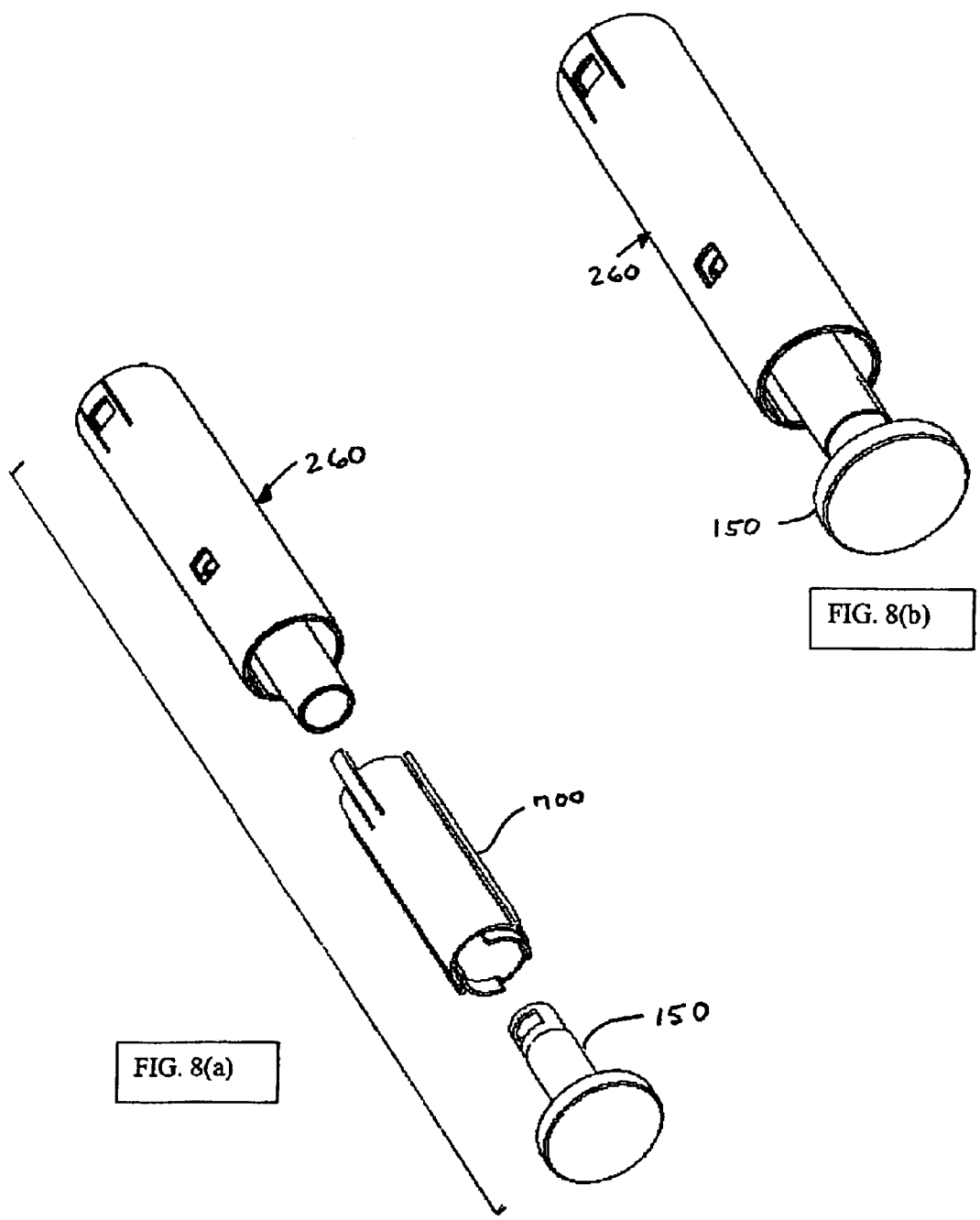

AUTOINJECTOR WITH EXTENDABLE NEEDLE PROTECTOR SHROUD

BACKGROUND OF THE INVENTION

1. Field of the Invention

The present invention relates to an autoinjector syringe for administering a beneficial agent to a patient. Particularly, the present invention is directed to a syringe including a spring-activated plunger and a spring deployed extendable shroud in combination with a needle or similar penetrator.

2. Description of Related Art

The use of a sharp-pointed piercing element, such as a syringe needle or the like, entails the risk of accidental needle sticks. To avoid such accidents, a variety of safety systems are known and available to protect the user of a syringe.

A first type of safety system includes a rigid cylindrical safety shield arranged to telescope over the syringe barrel. Such a shield can be moved between a retracted position to expose the syringe needle for use, and an extended position to surround the needle with the shield. For example, U.S. Pat. No. 6,419,658, U.S. Pat. No. 6,322,540, U.S. Pat. No. 6,319,234, U.S. Pat. No. 6,319,233, U.S. Pat. No. 4,425,120, U.S. Pat. No. 4,573,976, U.S. Pat. No. 4,850,994 and U.S. Pat. No. 4,923,447 disclose various extendable shield systems for a hypodermic syringe. It is ordinarily desirable to lock the needle shields in the protected position, and a number of prior art designs provide for such locked conditions. Furthermore, some systems, such as those disclosed in U.S. Pat. No. 5,201,708, U.S. Pat. No. 5,242,240 and U.S. Pat. No. 5,318,538 are also designed to allow the shields to be retracted from their locked, extended positions.

The above-described device using a spring loaded sheath can be disadvantageous because the spring and shroud are generally mounted on the outside of the syringe barrel and are thereby vulnerable to mechanical interference with foreign objects. Moreover, such devices are manually deployed, which is not particularly conducive for self-administering medication by those who suffer from arthritis or similar ailments that limit digital dexterity.

Another type of safety system has been developed for use with a device commonly referred to as an autoinjector. An autoinjector is generally a syringe configured to automatically extend a needle and inject a beneficial agent into a patient when a button or similar actuator is deployed. Hence, it is known for some autoinjectors to be configured to retract the needle into the housing of the device when the injection is complete. Devices of this type are described, for example, in U.S. Pat. No. 6,099,503, U.S. Pat. No. 5,779,677, and U.S. Pat. No. 5,300,030. These types of devices are advantageous because only a single hand is needed to complete an injection. Furthermore, the needle can be configured to be extendable such that the syringe needle is not normally visible to the user before or after the injection. This is advantageous for self-administered drug therapy.

Such conventional methods and systems generally have been considered satisfactory for their intended purpose. However, the autoinjector described above can not be used for its intended purpose if the mechanism that returns the needle into the housing should fail for some reason. Stated another way, if the needle does not retract automatically, the user has no safe means of covering the needle point.

There thus remains a continued need for an efficient and economic method and system for automatically injecting a beneficial agent that is easy to use and helps prevent against accidental needle sticks after use.

SUMMARY OF THE INVENTION

The purpose and advantages of the present invention will be set forth in and apparent from the description that follows, as well as will be learned by practice of the invention. Additional advantages of the invention will be realized and attained by the methods and systems particularly pointed out in the written description and claims hereof, as well as from the appended drawings.

To achieve these and other advantages and in accordance with the purpose of the invention, as embodied and broadly described, the invention is directed to a syringe including a housing having a proximal end and a distal end. The housing has a reservoir disposed therein. The syringe also includes a plunger to be received by the reservoir. The plunger is moveable between a first plunger position and a second plunger position. A plunger spring is also provided to urge the plunger toward the second plunger position when the plunger spring is deployed. The plunger spring can be deployed by an actuator. The syringe also includes a needle or similar penetrator proximate the distal end of the housing. Also provided is a shroud coupled with the housing. The shroud is moveable between a retracted position and an extended position. The shroud surrounds at least a portion of the needle when in the extended position. A shroud spring is biased to urge the shroud toward the extended position when the shroud spring is deployed. Further, an interlocking assembly in communication with the shroud is provided. The interlocking assembly has a first condition to maintain the shroud in the retracted position and a second condition to deploy the shroud spring and allow movement of the shroud toward the extended position.

Preferably, the interlocking assembly can be coupled with the plunger so as to be switched from the first condition to the second condition when the plunger is moved to the second plunger position. For example, the interlocking assembly can include at least one flexible tab provided on the shroud and an engagement surface provided on the plunger, whereby the engagement surface flexes the tab when the plunger is moved to the second plunger position. Alternatively, the interlocking assembly can include a switch operable from outside the housing to manually switch the interlocking assembly from the first condition to the second condition.

In accordance with a further aspect of the invention, the actuator can include an engagement element to retain the plunger in the first position. The engagement element acts to release the plunger and thus deploy the plunger spring when the actuator is actuated. In a preferred embodiment, the plunger spring can be a mechanical spring element although known springs, such as hydraulic or pneumatic, can be used. The syringe can further comprise a removable cover positioned on the distal end of the housing before the syringe is used.

Optionally, the needle is caused to be in fluid communication with the reservoir when the plunger is moved toward the second plunger position.

Additionally, the needle can be displaceable from a first needle position to a second needle position, such that the point of the needle extends from the housing when in the second needle position. The needle thus can be moved to the second needle position when the plunger is moved from the first plunger position toward the second plunger position.

Alternatively, and in accordance with a further aspect of the invention, the needle can be secured to the reservoir and the reservoir can be displaced with the needle.

In accordance with a further aspect of the invention, the syringe is provided with at least one guide element to provide registration between the reservoir and the plunger. The at least one guide element has a proximal end and a distal end. In one embodiment of the invention, the distal end of the guide element is fixedly attached to a mounting element that surrounds the reservoir. The mounting element is attached at a desired location along the reservoir, such as the proximal end of the reservoir. The mounting element may also be attached at the distal end of the reservoir.

Additionally, a locking assembly configured to inhibit movement of the shroud when moved to the extended position can also be provided. The locking assembly can include a protuberance to be received by a corresponding recess.

The invention also includes a method that includes providing a syringe as described above; loading a beneficial agent in the reservoir of the syringe; positioning the needle of the syringe at an injection site of a patient; moving the plunger toward the second plunger position to dispense the beneficial agent from the reservoir through the needle; and switching the interlocking assembly to the second condition to deploy the shroud spring and allow movement of the shroud toward the extended position. Optionally, the movement of the shroud toward the extended position provides an indication to a patient that beneficial agent has been injected.

It is to be understood that both the foregoing general description and the following detailed description are exemplary and are intended to provide further explanation of the invention claimed.

The accompanying drawings, which are incorporated in and constitute part of this specification, are included to illustrate and provide a further understanding of the syringe and method of the invention. Together with the description, the drawings serve to explain the principles of the invention.

BRIEF DESCRIPTION OF THE DRAWINGS

FIGS. 4(a)–4(d) are a cross-sectional side views depicting steps of a method of using a second representative embodiment of the syringe in accordance with the invention.

FIG. 8(a) is an exploded perspective view of a proximal portion of the second representative embodiment of the syringe of FIG. 4 in an unassembled state.

FIG. 8(b) is an exploded perspective view of a proximal portion of the second representative embodiment of the syringe of FIG. 4 in an assembled state.

DETAILED DESCRIPTION OF THE PREFERRED EMBODIMENT

Reference will now be made in detail to the present preferred embodiments of the invention, examples of which are illustrated in the accompanying drawings. The method and corresponding steps of the invention will be described in conjunction with the detailed description of the apparatus. The methods and apparatus presented herein can be used for injecting beneficial agents into a patient. The present invention is particularly suited for the self-administration of beneficial agents, particularly in the case of those who suffer from debilitating diseases, such as arthritis or the like. In accordance with the invention, it is possible and desired to provide an autoinjector mechanism that simplifies the complete injection cycle involving a sharp needle tip, and concludes with a shroud positioned about the needle tip to protect the user and others from the needle tip. This is of particular advantage where a user suffers from arthritis, and has limited digital dexterity.

Figure 1:
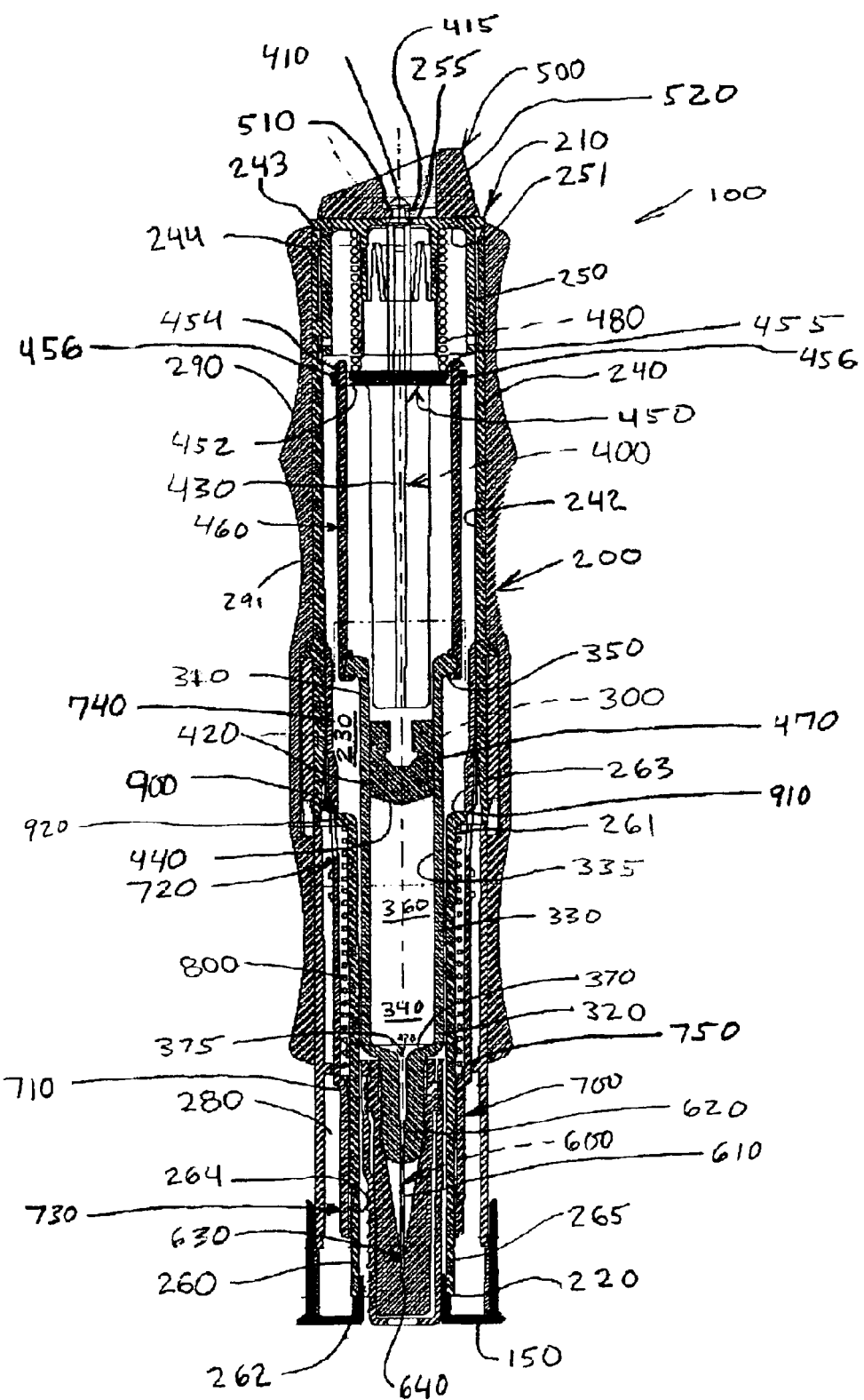
FIG. 1 is a cross-sectional side view of a first representative embodiment of the syringe in accordance with the present invention.

For purpose of explanation and illustration, and not limitation, an exemplary embodiment of the syringe in accordance with the invention is shown in FIG. 1 and is designated generally by reference character 100. This exemplary embodiment is also depicted in FIGS. 2(a)–2(e). Additional embodiments are shown in FIGS. 4–9 for purpose of illustration and not limitation.

Generally, a syringe includes a tubular body and a needle having a needle point. For example, and for purpose of illustration only, FIG. 1 shows a syringe 100 in accordance with the invention having a housing 200, a reservoir 300, a plunger 400, a plunger spring 480, an actuator 500, a needle 600 and an interlocking assembly 900. Alternative embodiments or variations of a syringe also are suitable for the present invention as will be recognized from the description below. Additionally, although not necessary, a removable cover 150, can be provided for the syringe 100, as shown in FIG. 1.

The syringe 100 of the present invention can be provided with a beneficial agent contained in the reservoir prior to syringe distribution. The syringe is preferably provided in a "loaded" condition ready for use. Preferably, the syringe also has a guard when distributed. The guard protects the actuator from accidental deployment of the syringe. The syringe 100 can therefore be distributed with the needle disposed in a first needle position inside the housing with the removable cover covering the needle. In preparation for injection, the removable cover is removed and the syringe is positioned at an injection site of a patient. The actuator is then actuated, thereby deploying the plunger spring. The plunger spring causes the plunger, reservoir and needle to advance distally from the actuator, and the needle pierces the skin of the patient. The plunger spring continues to push on the plunger, causing the contents of the reservoir to be dispensed into the patient. After the reservoir has been evacuated, the shroud is deployed. The deployment of the shroud is an indication to the user that the injection cycle has completed. The user then removes the syringe needle from the skin by pulling the syringe 100 away from the injection site. Once pulled away from the patient's skin, the shroud fully extends to a fully extended position and snaps into place, covering the needle point. Advantageously, the user is inhibited from seeing the needle point throughout the procedure.

In accordance with the present invention, the syringe device includes a housing to contain a reservoir, and if desired, a needle before the syringe is used.

For example and not for purposes of limitation, FIG. 1 depicts a housing 200 as embodied herein; the housing having a proximal end 210 and a distal end 220. As embodied herein, the housing 200 has a generally tubular exterior wall portion 240 and a generally tubular interior wall portion 260. An optional outer grip layer 290 can be formed around exterior wall portion 240. Grip layer 290 preferably has recessed portions 291 that enable secure gripping by a user. Interior wall portion 260 is preferably, but not necessarily, disposed concentrically inside exterior wall portion 240. Interior wall portion 260 has a proximal end 261 and a distal end 262. As embodied herein, the proximal end 261 of interior wall portion 260 has an outwardly projecting portion 263 integrally formed therewith.

The interior surface 264 of interior wall portion 260 and the interior surface 242 of exterior wall portion 240 collectively define a hollow, cylindrically shaped cavity 230. An additional, annularly shaped cavity 280 is defined by the interior surface 242 of exterior wall portion 240 and the exterior surface 265 of interior wall portion 260.

A variety of alternative configurations and structures can be used for housing 200. Interior wall portion 260 and exterior wall portion 240 can be separate pieces as described above or can be integrally formed as a single unit. If formed as separate pieces, interior wall portion 260 and exterior wall portion 240 can be attached to one another by way of machine threads, adhesive bonding, solvent welding, or any other way as known to those skilled in the art. For example, and with reference to FIG. 6, exterior wall portion 240 can be secured to interior wall portion 260 together by way of interlocking tabs 245 and openings 244. Interior and external wall portions 260, 240 are preferably formed of a plastic material, but can also be formed from any other suitable material, such as metal and/or composite materials. Additionally, in some applications housing 200 can alternatively be configured such that shroud 700 moves around the outside thereof instead of inside the housing 200. This is advantageous when sheath 700 is to be actuated manually with or without the presence of shroud spring 800. The housing 200 as embodied herein is provided with a cylindrical shape, having a generally circular cross-section. If desired, however, the housing can be provided with an elliptical or generally rectangular cross section, or any other cross section that permits operation of the syringe.

The exterior wall portion 240 has a proximal end opening 243 at its proximal end 244, to which an end cap 250 can be attached. The cavity 230 is thus configured to house a reservoir 300, a plunger 400, a plunger spring 480, and if desired, a needle 600, to be described in detail below.

In accordance with the present invention and as noted above, the syringe includes a reservoir disposed inside the housing to contain a beneficial agent.

For example and not for purposes of limitation, FIG. 1 depicts a reservoir 300 as embodied herein, having an open proximal end 310 and a distal end 320. The reservoir 300 includes a generally tubular wall 330, preferably made of plastic, glass, or similar material so as to define a chamber 340 therein. The wall 330 preferably terminates at the proximal end 310 of the reservoir 300 with an outward projection 350, such as an annular lip or a plurality of tabs, to prevent the proximal end 310 of the reservoir 300 from advancing distally beyond the outwardly projecting portion 263 of the proximal end 261 of interior wall portion 260. The distal end of the reservoir 300 is configured for fluid communication with a needle. For example, and as depicted in FIG. 1, the distal end 320 includes a wall defining a needle mounting hub 390 with an orifice 375 defined therethrough.

A variety of alternative configurations and structures can be used for reservoir 300. For example, and with particular reference to FIG. 9, the reservoir 300 can be configured substantially as described above, except that a frangible membrane can be provided at the distal end of the reservoir so as to burst upon the application of sufficient pressure with the chamber. Alternatively, the beneficial agent 360 can be contained within a frangible cylindrical cartridge 380 housed inside the chamber. In this embodiment of the invention, a proximal end 620 of the needle 600 extends past the distal end wall 370 located at the distal end 320 of the reservoir 300 and into the chamber 340. The proximal end 620 of the needle 600 is sufficiently sharp to pierce the frangible cartridge 380 when the cartridge 380 is pressed against the proximal end 620 of the needle 600, for example, by the face 440 of the plunger 400. This establishes fluid communication between the beneficial agent 360 contained in the cartridge 380 and the needle 600. Alternate embodiments of frangible membranes are disclosed in U.S. Pat. No. 4,983,164, the disclosure of which is expressly incorporated by reference herein.

The beneficial agent 360 is provided in a form that is conducive to being delivered through a needle, such as liquid form. Any beneficial agent can be used that is appropriate for use with a syringe.

In accordance with the present invention, the syringe also includes a plunger disposed inside the housing.

As seen in the exemplary embodiment in FIG. 1, the plunger 400 extends through an opening 255 in the end cap 250 of the housing 200. The plunger has a distal end 420 having a face 440, a shaft 430 and a proximal end 410. As embodied herein, a platform 450 is formed around on shaft 430 of the plunger. The platform 450 optionally defines openings 452 on opposite sides 454, 455 thereof, each to receive a guide element in the form of, for example, a rail 460. The rails 460 act to guide the platform 450 as the plunger 400 travels in a distal direction to dispense beneficial agent 360 from the reservoir. The plunger face 440 is configured to form at least a liquid-tight seal between the outer surface 470 of the plunger 400 and the inner surface 335 of tubular wall 330 of the reservoir 300. The plunger 400 can be further configured to include a mating surface 415 at its proximal end 410. The mating surface 415 is configured to mate with an engagement element 510 on actuator 500, as described in detail below.

A variety of alternative configurations and structures can be used for plunger 400. For example, the plunger can be made from more than one piece, such as a rigid shaft 430 and a more flexible end 420, or can be integrally formed as a single part. Plunger 400 can be made from any suitable materials such as metal or fiber reinforced composites, although plastic is preferred. Plunger 400 can also constitute a hollow, tubular member to permit filling of the reservoir 300 with a beneficial agent 360. In accordance with this alternative embodiment, a passage (not shown) defined through plunger 400 can have a one-way valve (not shown) disposed therein to permit flow into the reservoir 300 through the passage, but not in the opposite direction. A separate bleed line (not shown) can be provided or desired if necessary.

In further accordance with the present invention, the syringe also includes a plunger spring preferably disposed inside the housing.

As seen in the exemplary embodiment in FIG. 1, the plunger spring 480 is disposed around the shaft 430 of the plunger 400, and is biased to urge the plunger 400 in a distal direction with respect to the housing 200. The plunger spring 480 is maintained in a compressed condition before use of the syringe between the platform 450 and interior surface 251 of end cap 250, as a result of the mating surface 415 of the plunger being in engagement with the engagement element 510 on the actuator 500. When the mating surface 415 is not engaged with the engagement element 510, the plunger spring 480 acts to move the distal end 420 of the plunger 400 distally within the reservoir 300.

In a preferred embodiment of the present invention, the reservoir 300 is configured to move distally inside the housing 200. In this manner, and with the needle 600 mounted at the distal end 320 of the reservoir 300, the needle 600 is extended from the housing 200 by moving the reservoir 300 in a distal direction. If the proximal end 620 of the needle 600 is attached to the distal end 320 of the reservoir 300, the plunger spring 480 acts to move plunger 400, reservoir 300 and needle 600 distally until the limit tab(s) 350 of reservoir 300 come into physical contact with the outwardly projecting portion 263 of the proximal end 261 of interior wall portion 260. After this occurs, the plunger spring 480 continues to press against the plunger 400, causing the plunger 400 to move distally along one or more guide elements, or as embodied herein, rails 460 and, in the process, evacuate beneficial agent 360 from the reservoir 300 through the needle.

A variety of alternative configurations and structures can be used for plunger spring 480. While a compressive spring has been illustrated, any mechanical or electromechanical means of selectively urging the plunger in a distal direction are within the spirit and scope of the invention. For example, a tensile spring can be used that is biased to pull the plunger 400 in a distal direction instead of pushing it. Likewise, a pneumatic device including a cartridge containing a compressed gas could be used to cause the plunger to move and evacuate beneficial agent 360 from reservoir 300. In selected applications, an electromagnetic solenoid could also potentially be used to exert such a force.

Figure 10:
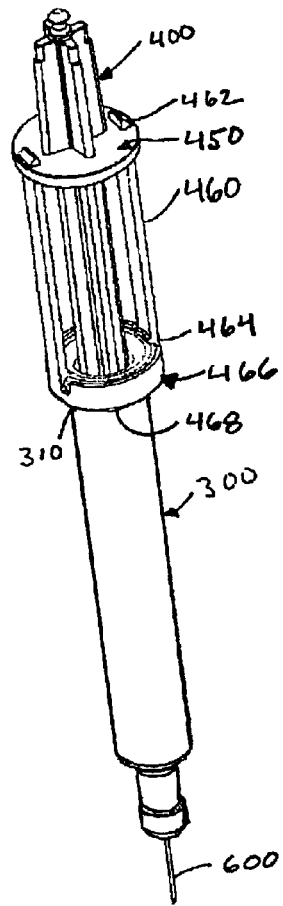
FIG. 10 is a perspective view of the selected components of FIG. 1.
Figure 11:
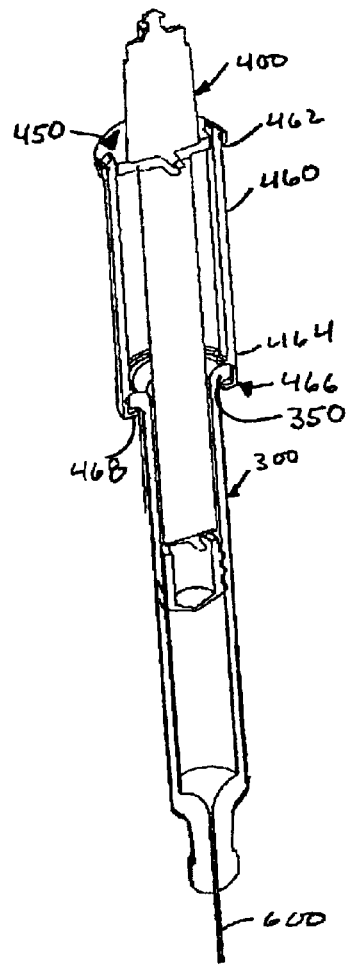
FIG. 11 is a perspective cross-sectional view of selected components of the embodiment of FIG. 1.

Further in accordance with the invention, the syringe is provided with at least one guide element for registration between the reservoir 300 and the plunger 400. For example, and as shown in the embodiment of FIGS. 1 and 10–11, the guide member can include one or more rails 460. The rails 460 each have a proximal end 462 and a distal end 464. The proximal end 462 of each rail is engaged with platform 450. The distal end 464 of each rail is attached to a mounting element 466 or similar mounting structure (such as clips) that surrounds the reservoir 300.

Figure 7A:
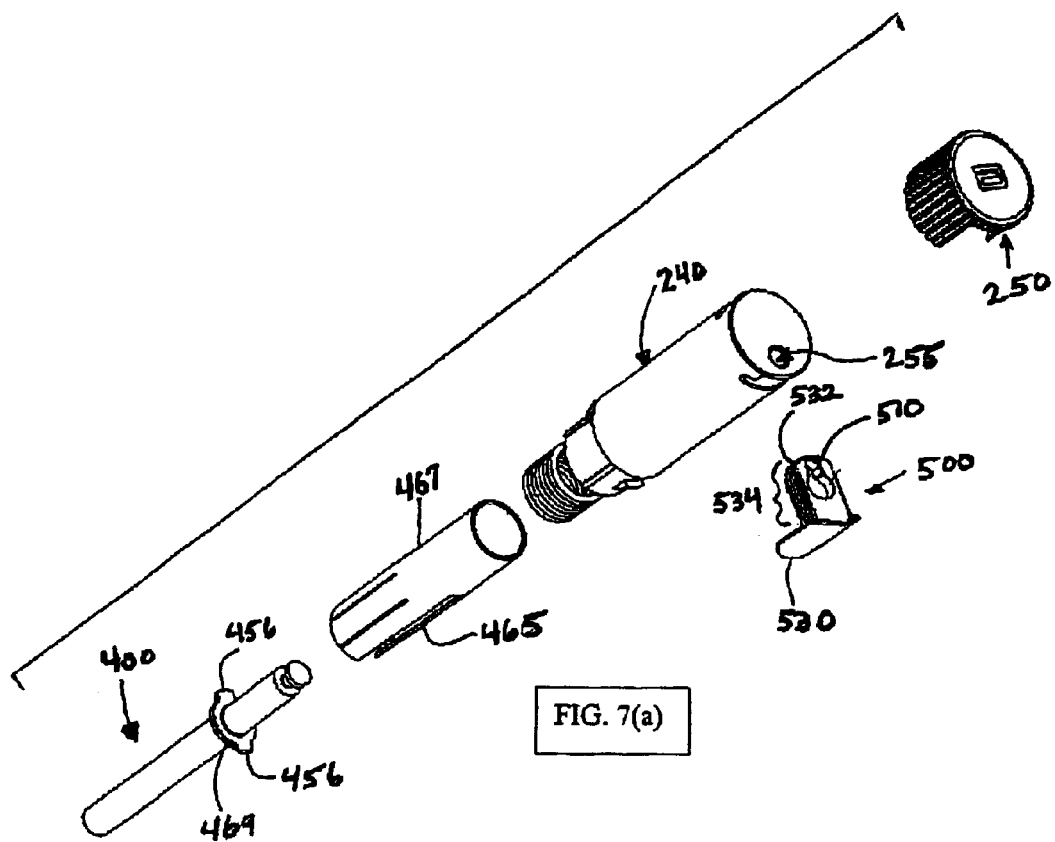
FIG. 7(a) is an exploded perspective view of a distal portion of the second representative embodiment of the syringe of FIG. 4 in an unassembled state.
Figure 7B:
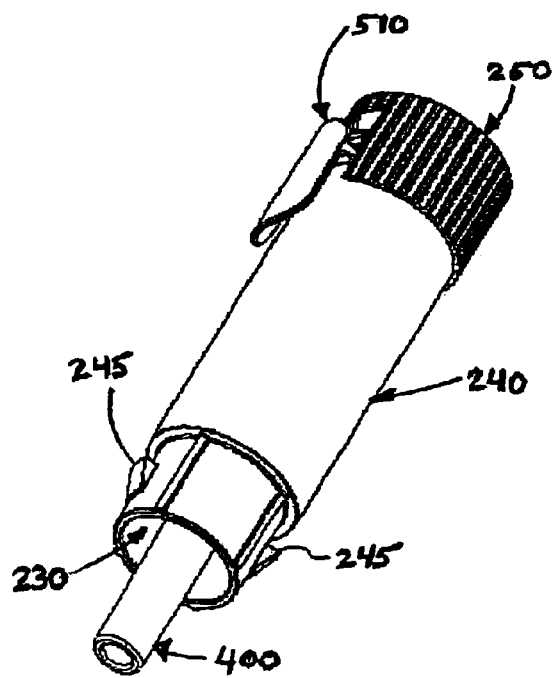
FIG. 7(b) is an exploded perspective view of a distal portion of the second representative embodiment of the syringe of FIG. 4 in an assembled state.

Alternatively, and as shown in the embodiment of FIG. 7(*a*), guide elements can be supplied in the form of recesses, or tracks 465 formed into guide structure 467 instead of rails 460 tracks 465 provide registration between protrusions 469 on which engagement surfaces 456 are formed and the guide structure 467. This provides alignment between plunger 400 and reservoir 300 (See also FIG. 4(*b*)).

As embodied herein, the mounting element 466 can be configured to surround the proximal end 310 of the reservoir 300. In this manner, mounting element 466 engages outward projection 350 when the plunger spring 480 is deployed to advance the reservoir 300, needle 600, mounting element 466 and rails 460 in a distal direction until the distal face 468 of mounting element 466 contacts outwardly projecting portion 263 of housing 200 as depicted, for example, in FIG. 2(*c*).

Figure 12:
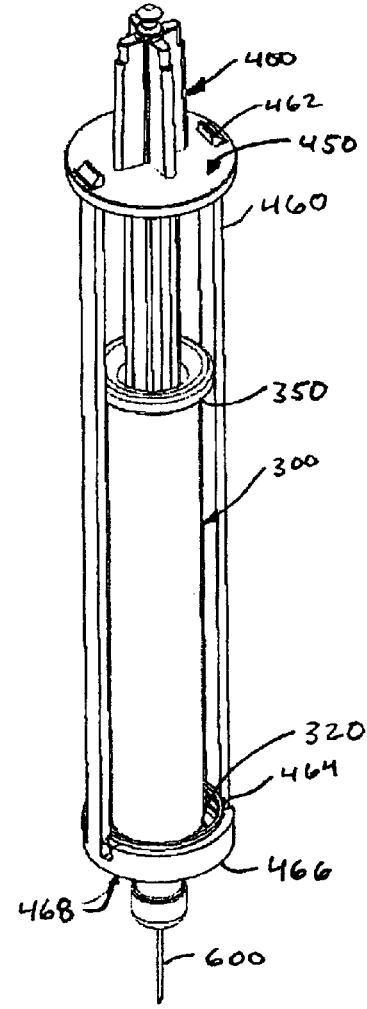
FIG. 12 is a perspective view of selected components depicting another embodiment of the syringe in accordance with the invention.

Alternatively, the mounting element 466 can be configured to engage any location along the length of the reservoir 300. For example, as shown in FIG. 12, mounting element 466 can engage the distal end 320 of the reservoir 300. The rails 460 of this embodiment would be increased in length accordingly. In this manner, mounting element 466 engages reservoir 300 when the plunger spring 480 is deployed to advance the reservoir 300, needle 600, mounting element 466 and rails 460 in a distal direction until the distal face 468 of mounting element 466 contacts a projection (not shown) at the distal end 220 of housing 200.

In further accordance with the present invention, the syringe also includes an actuator disposed at the proximal end of the housing for actuating the syringe to inject a beneficial agent.

As embodied in FIG. 1, the actuator 500 is provided with engagement element 510 that mates with mating surface 415 on the proximal end 410 of plunger 400. The actuator 500 is in direct physical contact with the end cap 250 of housing 200, and is configured to slide along a direction generally transverse to a longitudinal direction of the housing. The actuator 500 further can be provided with a digit interface surface 520 for a user to press so as to move the engagement element 510 out of engagement with the mating surface 415. In this manner, the plunger spring 480 is released and deployed to actuate the syringe 100. The actuator 500 can optionally ride in a track (not shown) in the end cap 250 to facilitate sliding movement, and a guard or lock (not shown) can be provided to prevent sliding movement of the actuator.

Alternatively, and as shown in the second embodiment of FIGS. 4 and 7(*a*), the end cap 250 can at least partially cover the actuator 500 engagement element 510. In this second embodiment of the invention, the actuator 500 includes digit interface surface 520 formed on the surface of an enlarged member 530. The engagement element 510 is mounted on the terminal end 532 of an arm 534 fixably attached to the enlarged member 530. In this embodiment of the invention, the engagement element 510 defines a key-hole shaped slot having an arcuately shaped edge 540 that partially circumscribes the mating surface 415 on the proximal end 410 of the plunger 400. A guard or lock (not shown) can also be provided to prevent the actuator 500 from accidentally being moved resulting in deploying the syringe 100.

A variety of alternative configurations and structures can be used for actuator 500. While a mechanical switch has been shown in the drawings, it would also be possible for the actuator to be a frangible member, such that the frangible member can be ruptured by exerting digital pressure on the digit interface surface 520 of the actuator 500, thereby releasing the plunger 400. Such an embodiment would be advantageous where the device is intended for a single use.

In further accordance with the present invention, the syringe also includes a needle proximate the distal end of the housing. The needle is configured to be in fluid communication with the reservoir during deployment of the syringe.

Figure 2A:
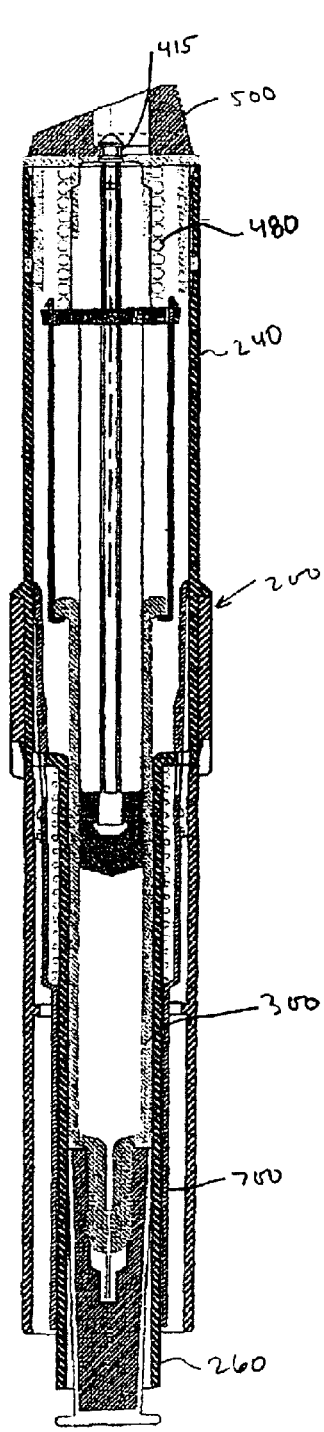
FIGS. 2(a)–2(e) are schematic views depicting steps of one method of using the syringe of FIG. 1 in accordance with the present invention.
Figure 2B:
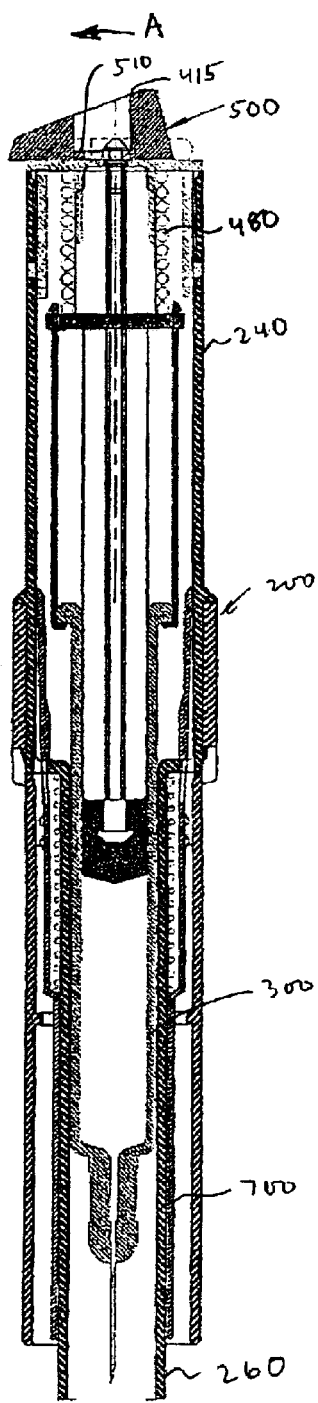
Figure 2C:
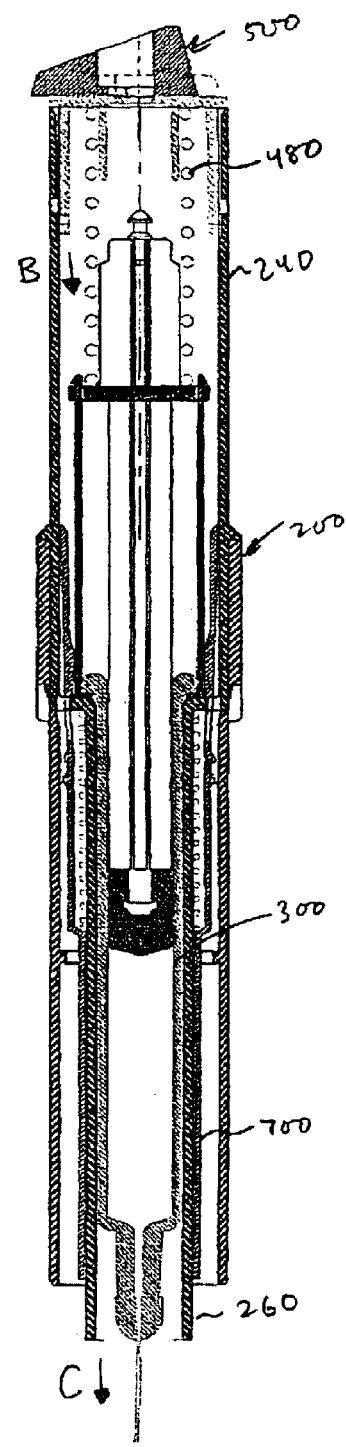

In a preferred embodiment, as shown in FIGS. 2(b)–2(c), the needle can be displaceable from a first needle position to a second needle position. The needle has a needle point that extends from the housing when the needle is in the second needle position.

As embodied in FIG. 1, the needle 600 has a proximal end 620, an elongate tubular shaft 610 and a needle point 640 at a distal end 630 thereof. The needle 600 can be sized and constructed according to conventional techniques. The needle 600 can be a separate assembly from the reservoir 300 or can be fitted into the distal end 320 of the reservoir 300. The proximal end 620 of the needle 600 is preferably in constant fluid communication with the distal end 320 of the reservoir 300. As embodied in FIGS. 1 and 2(b), the needle has a first needle position inside the housing 200. When the plunger spring 480 is deployed, needle 600 is moved to a second needle position, as shown in FIG. 2(c).

Optionally, the needle 600 can be configured to be in fluid communication with the reservoir 300 when the plunger 400 is moved toward the second plunger position.

Figure 9:
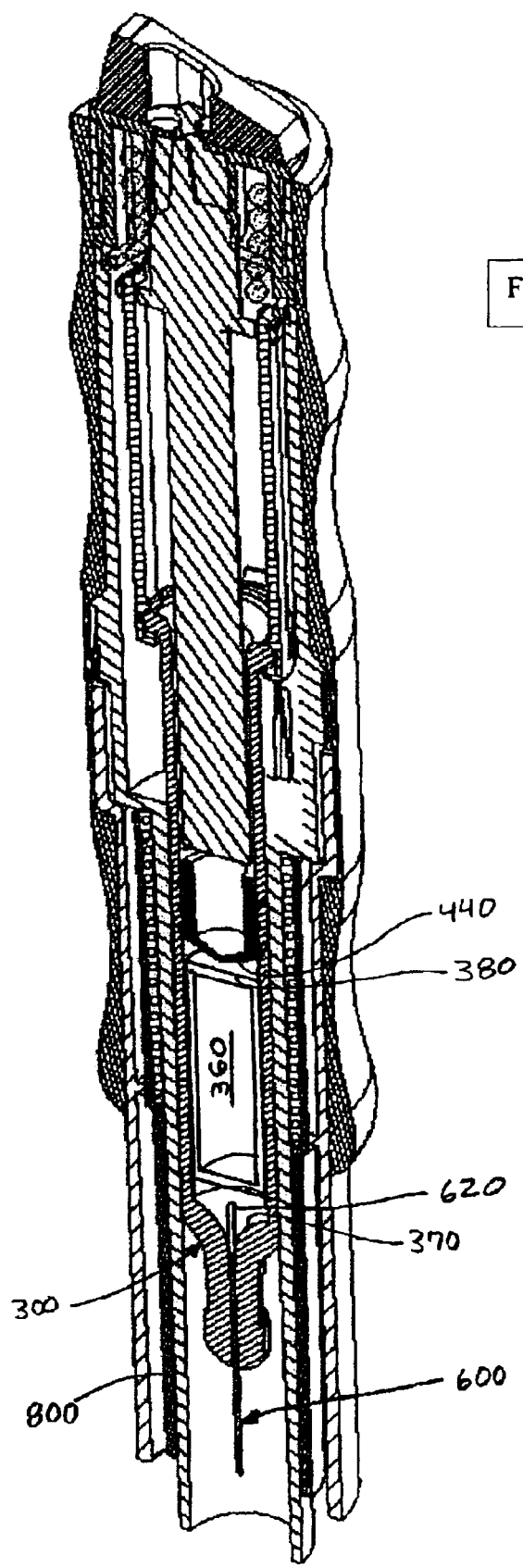
FIG. 9 is a perspective cross-sectional view of a third representative embodiment of the syringe in accordance with the invention.

For example, as shown in FIG. 9, the needle 600 can be configured for fluid communication with a beneficial agent 360 only upon deployment of the plunger 400. As embodied in FIG. 9, the needle 600 of FIG. 9 includes a sharpened proximal end 620 that pierces a frangible membrane of cartridge 380 containing a beneficial agent 360 when the syringe 100 is actuated by a user and the plunger spring 480 moves the face 440 of the plunger 400 in a distal direction, as previously described above.

Similarly, by way of further example, instead of using a cartridge 380 to isolate the beneficial agent from needle 600, it is also within the scope of the invention to provide reservoir 300 with a frangible membrane (not shown) near the proximal end 620 of the needle. In accordance with this aspect of the invention, when the plunger spring 480 deploys, the face 440 of the plunger increases the fluid pressure in the reservoir 300 by a predetermined amount sufficient to cause the membrane to rupture, thereby establishing fluid communication between the beneficial agent 360 and the needle 600.

In further accordance with the present invention, the syringe also includes a shroud coupled with the housing. The shroud is moveable between a retracted position and an extended position; the shroud surrounding at least a portion of the needle when in the extended position.

As embodied in FIG. 1, the shroud 700 includes a tubular wall portion 710 having a proximal end 720 and a distal end 730. Preferably, the shroud 700 also has a spring engagement element, such as spring engagement surface 750 depicted in FIG. 1 to engage with a shroud spring 800, as discussed in detail below. The cross-section of the shroud 700 preferably, although not necessarily, will be similar to that of housing 200, but will be sized to fit freely inside the inner surface of the housing 200.

Figure 2D:
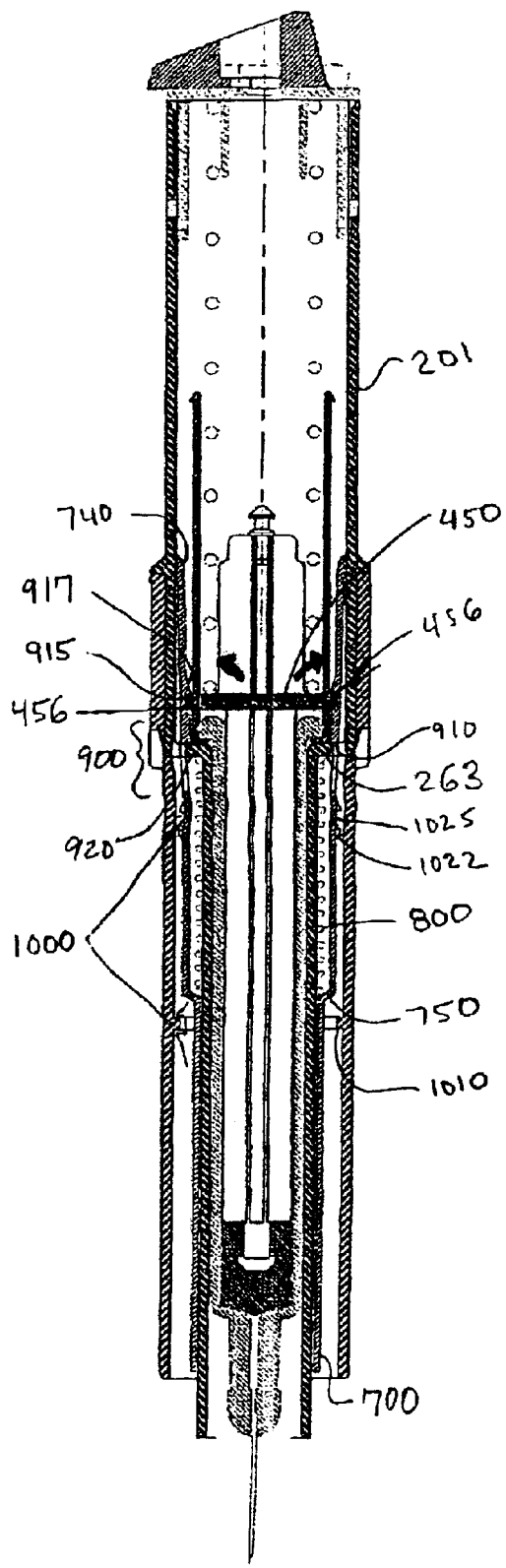
Figure 2E:
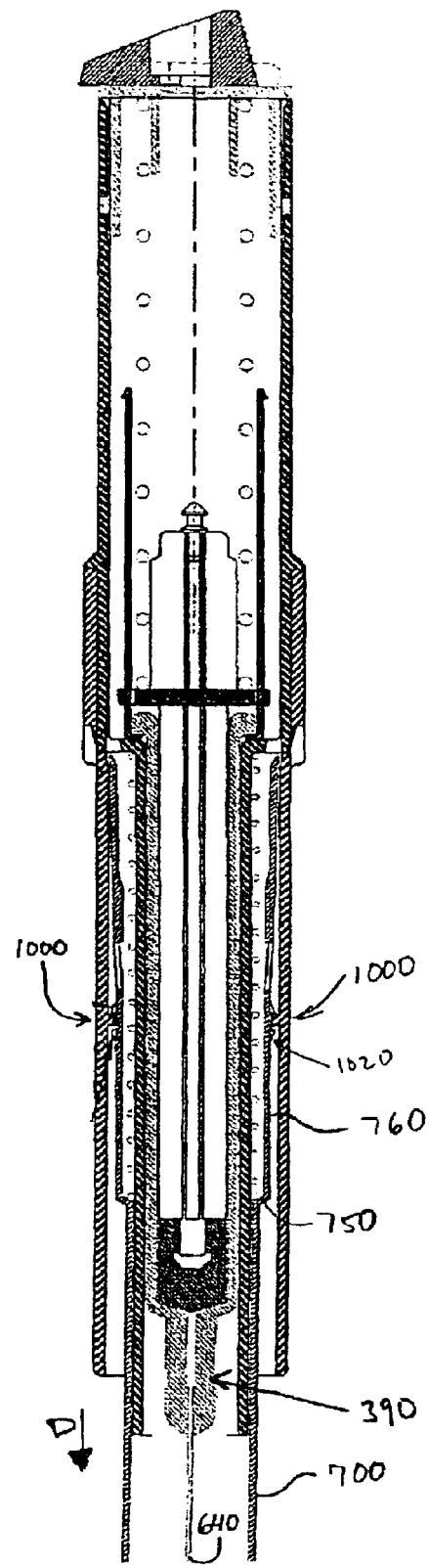

The shroud 700 as embodied herein is moveable between a retracted position and an extended position such that the shroud 700 surrounds the needle point 640 when shroud 700 is in the extended position. FIG. 2(d) shows shroud 700 in a retracted position. In its retracted position, shroud 700 preferably is wholly contained in annularly shaped cavity 280 of housing 200. Interlocking assembly 900, as discussed in detail below, maintains shroud in its retracted position. In its retracted position, shroud 700 is protected from interference with foreign objects that would impede its function. FIG. 2(e) shows shroud 700 in an extended position. In its extended position, shroud 700 is preferably locked in place by locking assembly, as discussed in detail below. As seen in FIG. 2(e) in its extended position, shroud 700 surrounds the needle 600, thus protecting the user from accidental needle sticks after syringe 100 has been used. In use, it is preferable that the shroud 700 be deployed before the syringe is taken away from the skin. The shroud 700 of the present invention is therefore configured to act as an indication to the user that the injection has completed. When the user pulls the syringe away from the skin of the patient, the shroud 700 will fully extend.

In further accordance with the present invention, the syringe also includes a shroud spring biased to urge the shroud from a retracted position toward an extended position when the shroud spring is deployed.

As embodied in FIG. 1, shroud spring 800 is a compressed mechanical spring, although any suitable spring can be used in a manner similar to plunger spring 480. The shroud spring 800 is biased to urge the shroud 700 toward the extended position when the shroud spring 800 is deployed. The shroud spring 800 is disposed within the shroud 700 and around the exterior surface 265 of interior wall portion 260 of the housing 200. In this manner, both the shroud 700 and the shroud spring 800 are protected from damage or interference with foreign objects. Preferably, the shroud spring 800 as embodied herein is a mechanical spring made of metal or plastic. Before the syringe 100 is used, the shroud 700 is initially in a retracted position, as shown in FIG. 2(d). In this position, shroud spring 800 is in a compressed state, held in place between spring engagement surface 750 and outwardly projecting portion 263 of interior wall portion 260.

A variety of alternative configurations and structures can be used for shroud 700 and shroud spring 800. For example, if desired, the shroud 700 can be configured to slide along the exterior of housing 200 (not shown). In accordance with this aspect of the invention, the shroud spring 800 preferably would be housed between the interior surface 770 of shroud 700 and the exterior surface 201 of housing 200. In this manner, shroud spring 800 is still protected from interference with foreign objects.

In further accordance with the present invention, the syringe also includes an interlocking assembly in communication with the shroud. The interlocking assembly has a first condition to maintain the shroud in the retracted position and a second condition to deploy the shroud spring and allow movement of the shroud toward the extended position.

Figure 3:
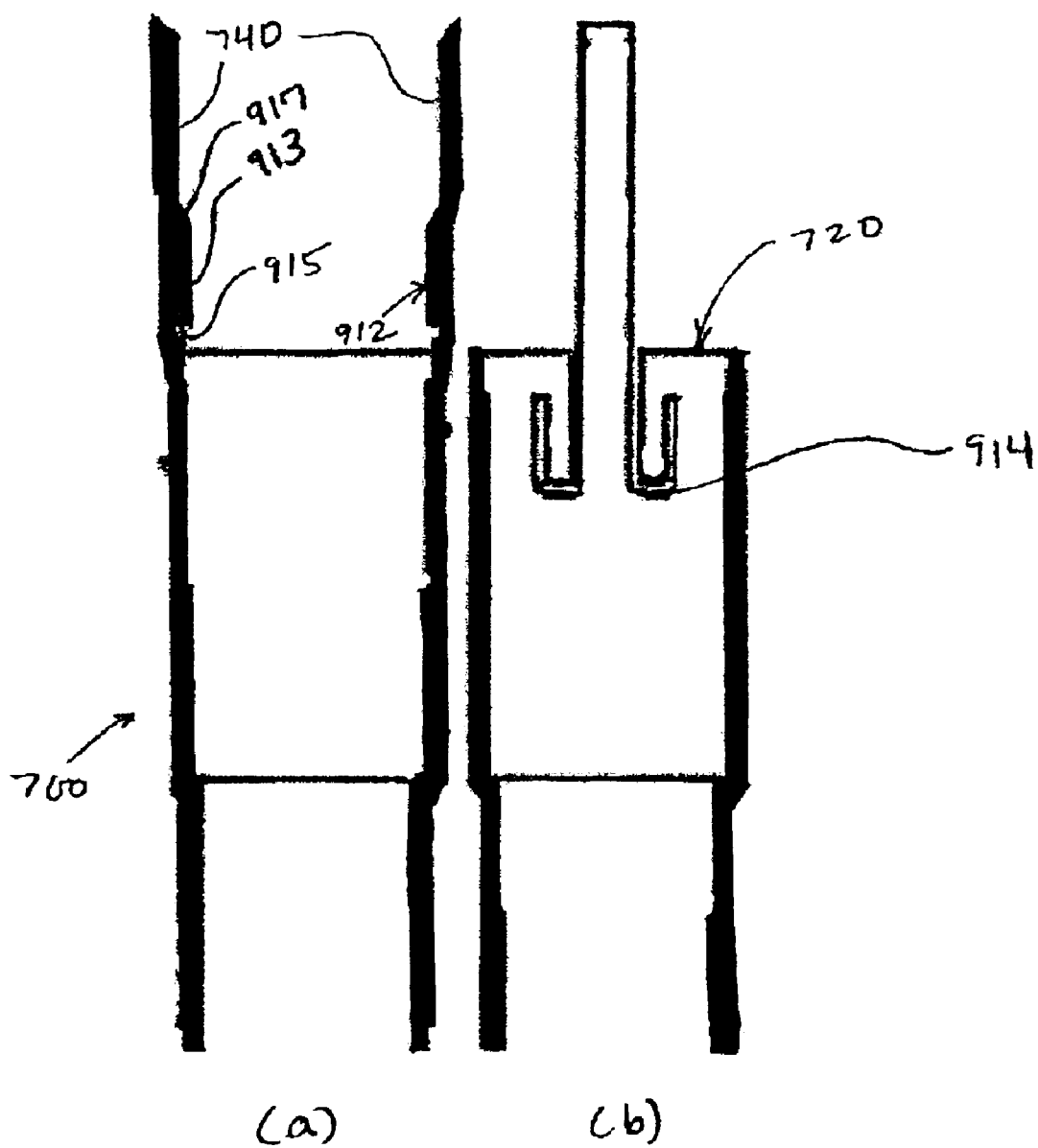
FIGS. 3(a)–3(b) are cross-sectional side views of the shroud of the syringe of FIG. 1.
Figure 5:
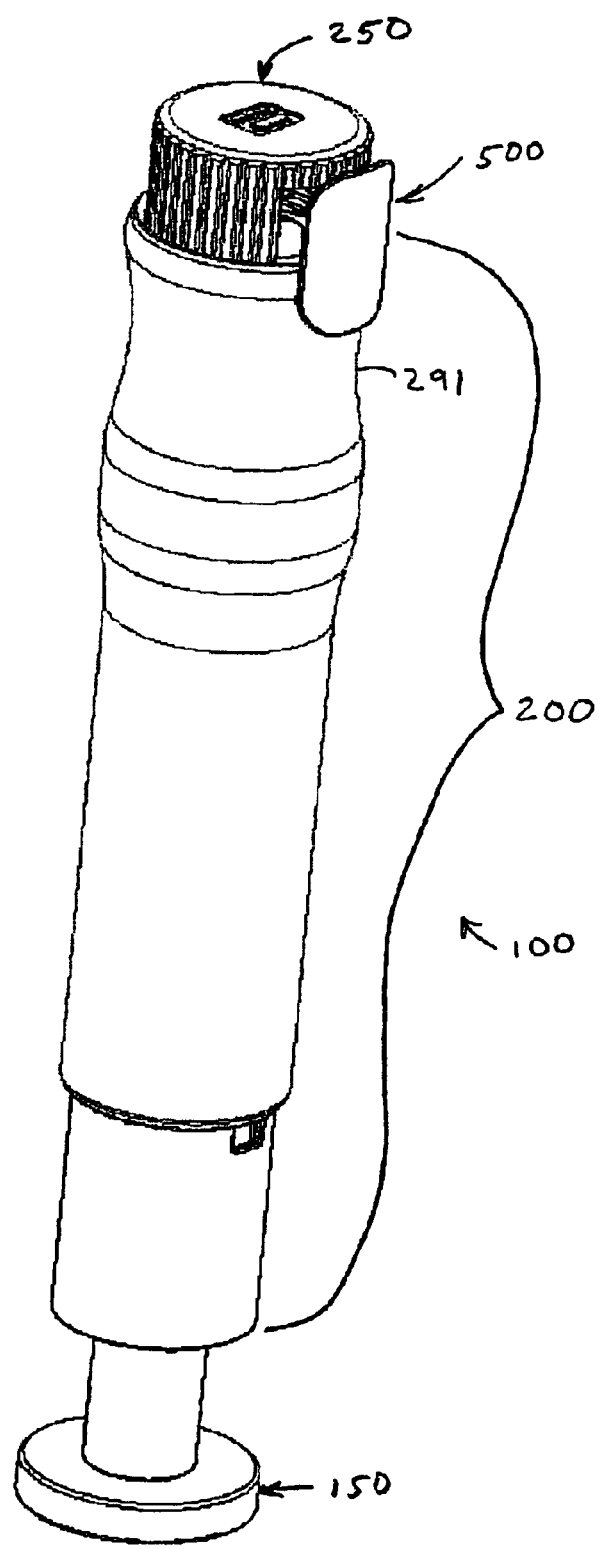
FIG. 5 is a perspective side view of the exterior of the second representative embodiment of the syringe of FIG. 4.

As embodied herein and with reference to FIGS. 2(d)–2(e) and FIG. 3, interlocking assembly 900 includes at least one interlocking element 910 configured for engagement with a corresponding first receiving portion 920. For example, and as embodied in FIGS. 2(d)–2(e) and FIG. 3, interlocking element 910 includes at least one flexible tab 740 extending proximately from the proximal end 720 of the shroud 700. The flexible tab 740 has an extension 912 with a seating surface 915 configured to engage with outwardly projecting portion 263 of interior wall portion 260. When shroud 700 is in a retracted condition as shown in FIG. 2(d), surface 915 seats on outwardly projecting portion 263 of housing 200, thus preventing shroud 700 from moving toward its extended position.

In accordance with a further aspect of the invention, the interlocking assembly is coupled with the plunger so as to be switched from the first condition wherein the shroud is maintained in the retracted position, to the second condition, wherein the shroud spring is deployed to allow movement of the shroud toward the extended position.

For purpose of illustration, and not limitation; the interlocking assembly embodied in FIGS. 1–3 is provided with cam surface 917. The cam surface is configured to be engaged by a corresponding engagement surface 456 provided on the plunger 480. After syringe 100 is actuated and the face 440 of the plunger 400 approaches a predetermined location proximate the distal end 320 of the reservoir 300, one or more engagement surfaces 456 on the periphery of platform 450 contact and bias tabs 740 outwardly. In this manner, the flexible tabs 740 will be flexed outwardly to disengage seating surface 915 from portion 263.

With reference to FIG. 3, distal tab 740 preferably is attached to shroud 700 at hinge point 914. Locating the hinge point 914 at a location distal to the proximal end 720 of shroud 700 permits a sufficient bending moment to be created by engagement surfaces 456 urging against receiving surfaces 913 so as to permit seating surfaces 915 to disengage with outwardly projecting portion 263. As a consequence, seating surface 915 is forced out of engagement with outwardly projecting portion 263 of interior wall portion 260 of housing 200. This release deploys shroud spring 800 against spring engagement surface 750, thereby pushing shroud 700 in a distal direction. If the movement of shroud 700 is unimpeded by the skin of the user, shroud 700 will fully extend to its extended position covering the needle point 640, as seen in FIG. 2(e). Preferably, however, the shroud 700 is extended against the skin of the patient so as to provide a tactile indication that the injection cycle is completed. As the needle is withdrawn from the injection site, it is automatically surrounded by the shroud 700. Interlocking elements 910 are preferably formed of an injection-molded plastic material that is sufficiently flexible to enable the interlocking elements 910 to flex for purposes of disengagement from outwardly projecting portion 263 of interior wall portion 260 of housing 200.

A variety of alternative configurations and structures can be used for interlocking assembly 900. For example, interlocking elements 915 can instead be frangible members configured to hold the shroud in its retracted position. These frangible members can be ruptured when the distal tabs 740 are splayed outwardly by engagement surfaces 456 on platform 450. In accordance with a different embodiment of the invention, and with reference to FIGS. 4 and 6, an alternative interlocking assembly 900 is shown. This interlocking assembly 900 works in a manner similar to the embodiment of FIG. 1. However, instead of having a cammed surface attached to the shroud that facilitates outward movement of flexible tabs 740, a cammed surface is provided on engagement surfaces 456. Distal movement of plunger thereby moves engagement surfaces 456 against the corner portions 741 of flexible tabs 740 to urge them outward, disengaging seating portions 915 from outwardly projecting member 263, thereby disengaging interlocking element 900. Shroud 700 is now free to move distally as described above with regard to the embodiment of FIGS. 1–3.

In accordance with another aspect of the invention, a locking assembly is also provided. The locking assembly is configured to inhibit movement of the shroud when the shroud is moved to an extended position.

As embodied herein and with reference to FIGS. 2(d) and 2(e), for purpose of illustration and not limitation, locking assembly 1000 includes locking element 1010, such as a ridge or annular bead, formed on the interior surface 242 of exterior wall portion 240 of housing 200. The locking element 1010 is configured to mate with a lock receiving portion 1020 that, as depicted in the first exemplary embodiment of the invention, is formed on the exterior surface 760 of shroud 700. As seen in FIG. 2(d), lock receiving portion 1020 has an inclined surface 1022, which acts as a ramp, to permit locking element 1010 to slide into an adjacent recess 1025 when the shroud 700 extends in a distal direction with respect to housing 200. After locking element 1010 has slid along the inclined surface 1022 of lock receiving portion 1020, it snaps into recess 1025. Shroud 700 is thus locked into place, and inhibited from further movement.

A variety of alternative configurations and structures can be used for locking assembly 1000. With reference to FIG. 4, in an alternative embodiment of the syringe in accordance with the invention, lock receiving portion 1020 defined as a recess in interior wall portion 260 of housing 200 and locking element 1010 is defined by interlocking element 910 as shown in FIG. 4. above. Alternatively, an adhesive or bonding surface (not shown) can be used in lieu of a snap-fit arrangement as described above. According to this alternative embodiment, a surface on the shroud is provided with a thin layer of adhesive or bonding material not in engagement with any other surface before the shroud 700 is deployed, but configured to contact and securely attach such of syringe 100 together when the shroud 700 is extended. By way of further example, lock receiving portions 1020 can have a small quantity of gel-type adhesive disposed in recess 1025 to form a strong mechanical bond with locking element 1010 after shroud 700 is deployed. As another example, the action of deploying the shroud can rupture a membrane between two small reservoirs built into the shroud (not shown) having contents that, when mixed, quickly expand and cure to form a voluminous foam that fills the interior space of the shroud 700, or otherwise form a secure bond to lock the shroud in place.

In accordance with another aspect of the invention, a syringe is provided wherein the interlocking assembly includes a switch operable from outside the housing to manually switch the interlocking assembly from the first condition to the second condition.

For purposes of illustration and not limitation, a syringe similar to that in FIG. 1 or FIG. 4(a) can be provided, but modified to be actuated manually if desired. A shroud spring can still be employed. However, rather than having interlocking assembly 900 be disengaged solely by movement of the plunger 400, syringe 100 can be configured to disengage interlocking assembly manually. For this purpose, a shroud actuator (not shown), similar to actuator 500, can be provided having an exterior portion with a digit interface surface and an arm or similar structure that can protrude through an opening (not shown) in the housing 200 and contact cam surface 917. When actuated by a user, the arm of shroud actuator disengages seating surface 915 from outwardly projecting portion 263 and allows shroud 700 to deploy under the force of shroud spring 800 as described above.

Reference will now be made to describe a representative method of using the present invention. The method of the present invention includes providing a syringe as described in detail above; loading beneficial agent into the reservoir of the syringe; positioning the needle of the syringe at an injection site of a patient; moving the plunger toward the second plunger position to dispense the beneficial agent from the reservoir through the needle; and switching the interlocking assembly to the second condition to deploy the shroud spring and allow movement of the shroud toward the extended position.

As embodied herein, and with specific reference to FIGS. 2(a)–2(e), the method of the present invention includes providing a device 100 as described in detail above.

Although the embodiment of FIG. 1 is shown in FIGS. 2(a)–2(e), any of the disclosed embodiments of the device are suitable for the method of the present invention. For example, a second representative embodiment of the invention is shown in FIGS. 4(a)–4(d).

In accordance with the method of the invention, beneficial agent is loaded into the reservoir of the syringe. The beneficial agent loading step can occur at any of a number of different times during the method. For example, in the case of a preloaded, disposable syringe, the beneficial agent loading step can occur during manufacture. The reservoir 300 can be directly injected with a beneficial agent 360 or loaded with a cartridge 380 containing beneficial agent 360 prior to assembly of syringe 100.

Figure 6:
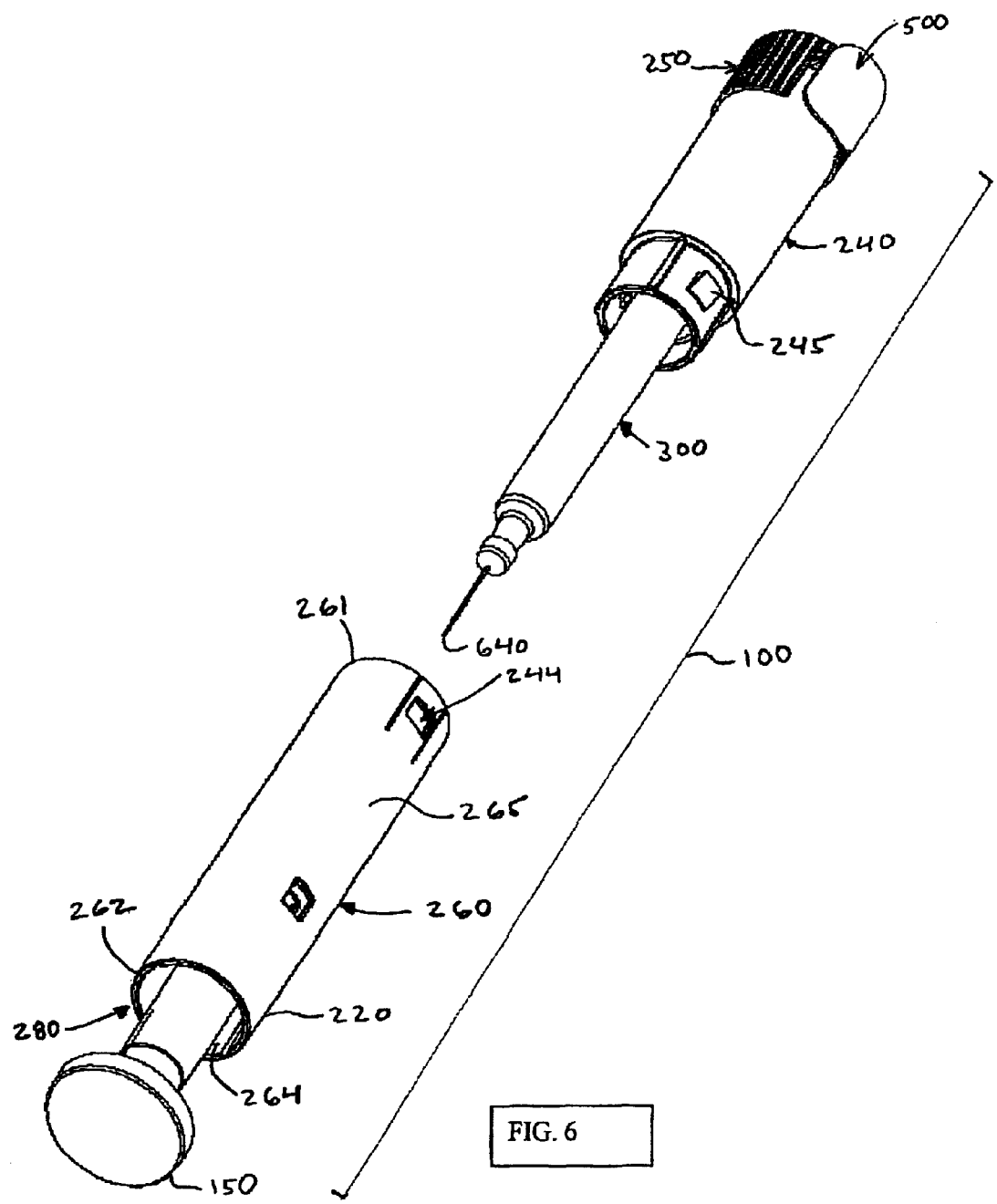
FIG. 6 is an exploded perspective view of the second representative embodiment of the syringe of FIG. 5.

Alternatively, such as when a cartridge 380 is used, syringe 100 could be configured to be loaded by a pharmacist or other medical personnel. This is particularly attractive, because the inert syringe can be kept in storage virtually indefinitely and loaded with a cartridge 380 containing fresh beneficial agent 360 when needed. To facilitate this embodiment, syringe 100 is configured such that it can be easily disassembled or sold in a disassembled condition to permit beneficial agent 360 to be introduced. For example, the syringe can be provided in two sections as shown in FIG. 6, which is easily loaded with a cartridge of beneficial agent and then snap fit together. As another option (not shown), syringe 100 can be configured with an opening through housing 200 to accept a cartridge 380 into reservoir 300. Syringe 100 also can be filled by configuring plunger 400 to include a hollow member that provides a hollow passage (not shown) spanning between the face 440 of plunger 400 and the proximal end 410 of plunger 400. As mentioned above, such a passage could be provided with a one-way valve (not shown) and accompanying bleed line to permit introduction of liquid beneficial agent 360 through the proximal end 410 plunger 400 into chamber 340 of reservoir 300 but prevent flow in the opposite direction. When a syringe 100 according to this embodiment of the invention is actuated, beneficial agent 360 will flow through the needle point 640 into the patient as described above instead of flowing backward through the passage due to the one way valve preventing any such flow.

In accordance with the method of the invention, the needle of the syringe is positioned at an injection site of a patient. The distal end of syringe 100 should be pressed firmly against the user's skin to ensure that the needle point 640 penetrates the skin of the patient without unnecessarily damaging the skin.

If provided, an actuator lock (not shown) covering the actuator 500 is preferably removed before the syringe positioning step. Once the actuator lock is removed, syringe 100 can be deployed to administer a beneficial agent.

In accordance with the method of the invention, the plunger is then moved toward the second plunger position to dispense the beneficial agent from the reservoir through the needle. As embodied herein and for purpose of illustration as depicted in FIGS. 2(a)–2(b) with respect to the embodiment of FIG. 1 (and as depicted in FIGS. 4(a)–4(b) with respect to the second representative embodiment), actuator 500 is moved as shown by arrow A to disengage engagement element 510 from mating surface 415 on the proximal end 410 of the plunger 400. The plunger spring 480 then causes the beneficial agent 360 to be injected as described above, and as shown in FIGS. 2(c)–2(d) with respect to the embodiment of FIG. 1 (see also FIG. 4(c) with respect to the second representative embodiment).

As further depicted in FIG. 2(c), and in accordance with another aspect of the invention, the needle is moved (as shown by arrow C) from a first needle position to a second needle position when the plunger is moved from the first plunger position toward the second plunger position. In accordance with this aspect of the invention, the needle has a needle point extending from the housing when in the second needle position. In further accordance with this aspect of the invention, the positioning step includes placing the distal end of the housing against the injection site.

In accordance with this aspect of the invention and as shown in FIG. 2(c), when the plunger spring 480 is released, it moves the reservoir 300 and the needle 600 in a distal direction, such that the point 640 of the needle 600 protrudes from the housing. Preferably, the positioning step will have occurred before the needle has moved to a point protruding from the housing for purposes of facilitating the injection. Using syringe 100 in this manner helps prevent unnecessary damage to the patient's skin.

In further accordance with the method of the invention, after the beneficial agent is introduced, the interlocking assembly is then switched from the first condition to the second condition to deploy the shroud spring and allow movement of the shroud toward the extended position. Preferably, the shroud 700 is deployed automatically, as described above and as shown by arrow D in FIGS. 2(d)–2(e). FIG. 4(d) shows the shroud 700 in a deployed position with regard to the second representative embodiment. Particularly, and with reference to the embodiment of FIG. 2(d), the interlocking assembly of the syringe provided by the providing step is coupled with the plunger so as to be switched from the first condition to the second condition when the plunger is moved to the second plunger position; and further wherein the switching step is performed by moving the plunger to the second plunger position. Alternatively, shroud 700 can be deployed manually. This would be particularly practical in an embodiment of the invention where the shroud 700 is configured to slide about the exterior of the housing 200. In accordance with such an alternative embodiment, the shroud 700 could be held in place by tabs engaged with receiving surfaces whereby the act of squeezing the shroud would act to release the shroud 700. After releasing the shroud, the user would advance the shroud until it snaps into place in an extended position covering the needle point 640, at which point it could optionally be locked using an interlocking assembly 900 as described above.

The syringe and method of using a syringe of the present invention, as described above and shown in the drawings, provide for a convenient way for a patient to self medicate, particularly, for example, where the patient has arthritis. Using any suitable material of construction, any of a number of known and conventional manufacturing techniques, such as injection or vacuum molding, can be employed to manufacture the syringe of the present invention. It will be apparent to those skilled in the art that various modifications and variations can be made in the method and system of the present invention without departing from the spirit or scope of the invention. Thus, it is intended that the present invention include modifications and variations that are within the scope of the appended claims and their equivalents.

What is claimed is:

1. A syringe comprising:

a housing having a proximal end and a distal end, the housing having a reservoir disposed therein;

a plunger to be received by the reservoir, the plunger being moveable between a first plunger position and a second plunger position;

a plunger spring configured to urge the plunger toward the second plunger position when the plunger spring is deployed;

an actuator to deploy the plunger spring;

a needle proximate the distal end of the housing, the needle in fluid communication with the reservoir;

a shroud coupled with the housing, the shroud being moveable between a retracted position and an extended position, the shroud surrounding at least a portion of the needle when in the extended position;

a shroud spring biased to urge the shroud toward the extended position when the shroud spring is deployed; and an interlocking assembly in communication with the shroud, the interlocking assembly having a first condition to maintain the shroud in the retracted position and a second condition to deploy the shroud spring and allow movement of the shroud toward the extended position.

2. The syringe of claim 1, wherein the actuator includes an engagement element to retain the plunger in the first position, the engagement element releasing the plunger to deploy the plunger spring when the actuator is actuated.

3. The syringe of claim 1, wherein the plunger spring is a mechanical spring element.

4. The syringe of claim 1, further comprising a cover to cover the distal end of the housing before the syringe is used.

5. The syringe of claim 1, wherein the needle is displaceable from a first needle position to a second needle position, the needle having a needle point extending from the housing when in the second needle position.

6. The syringe of claim 5, wherein the needle is configured to be moved from the first needle position to the second needle position when the plunger is moved from the first plunger position toward the second plunger position.

7. The syringe of claim 5, wherein the needle is secured to the reservoir, the reservoir being displaceable so as to displace the needle from the first needle position to the second needle position.

8. The syringe of claim 1, wherein the interlocking assembly is coupled with the plunger so as to be switched from the first condition to the second condition when the plunger is moved to the second plunger position.

9. The syringe of claim 8, wherein the interlocking assembly includes at least one flexible tab provided on the shroud and an engagement surface provided on the plunger, the engagement surface flexing the tab when the plunger is moved to the second plunger position.

10. The syringe of claim 1, wherein the interlocking assembly includes a switch operable from outside the housing to manually switch the interlocking assembly from the first condition to the second condition.

11. The syringe of claim 1, further comprising a locking assembly, the locking assembly configured to inhibit movement of the shroud when moved to the extended position.

12. The syringe of claim 11, wherein the locking assembly includes a protuberance to be received by a corresponding recess.

13. A syringe comprising:

a housing having a proximal end and a distal end, the housing having a reservoir disposed therein;

a plunger to be received by the reservoir, the plunger being moveable between a first plunger position and a second plunger position;

at least one guide element to provide registration between the reservoir and the plunger;

a plunger spring configured to urge the plunger toward the second plunger position when the plunger spring is deployed;

an actuator to deploy the plunger spring;

a needle proximate the distal end of the housing, the needle in fluid communication with the reservoir;

a shroud coupled with the housing, the shroud being moveable between a retracted position and an extended position, the shroud surrounding at least a portion of the needle when in the extended position;

a shroud spring biased to urge the shroud toward the extended position when the shroud spring is deployed; and an interlocking assembly in communication with the shroud, the interlocking assembly having a first condition to maintain the shroud in the retracted position and a second condition to deploy the shroud spring and allow movement of the shroud toward the extended position.

14. The syringe of claim 13, wherein the at least one guide element is a rail having a proximal end and a distal end, the distal end of the rail attached to a mounting element, the mounting element engaging the reservoir.

15. The syringe of claim 14, wherein the mounting element is a retaining ring.

16. The syringe of claim 14, wherein the mounting element surrounds a proximal end of the reservoir.

17. The syringe of claim 14, wherein the mounting element surrounds a distal end of the reservoir.

18. The syringe of claim 13, wherein the guiding element is a recess defined in a guide structure, and the recess is configured to receive a protrusion extending from the plunger.

19. A method of delivering a beneficial agent to a patient, the method comprising the steps of:

providing a syringe including
a housing having a proximal end and a distal end, the housing having a reservoir disposed therein,
a plunger to be received by the reservoir, the plunger being moveable between a first plunger position and a second plunger position,
a plunger spring configured to urge the plunger toward the second plunger position when the plunger spring is deployed,
an actuator to deploy the plunger spring,
a needle proximate the distal end of the housing for delivering beneficial agent from the reservoir to a patient,
a shroud coupled with the housing, the shroud being moveable between a retracted position and an extended position, the shroud surrounding at least a portion of the needle when in the extended position,
a shroud spring biased to urge the shroud toward the extended position when the shroud spring is deployed, and
an interlocking assembly in communication with the shroud, the interlocking assembly having a first condition to maintain the shroud in the retracted position and a second condition to deploy the shroud spring and allow movement of the shroud toward the extended position;

loading beneficial agent in the reservoir of the syringe;

positioning the syringe at an injection site of a patient;

moving the plunger toward the second plunger position to dispense the beneficial agent from the reservoir through the needle; and switching the interlocking assembly to the second condition to deploy the shroud spring and allow movement of the shroud toward the extended position.

20. The method of claim 19, wherein the needle is in fluid communication with the reservoir when the plunger is moved toward the second plunger position.

21. The method of claim 19, wherein the moving step includes actuating the actuator to deploy the plunger spring.

22. The method of claim 19, wherein the needle of the syringe provided by the providing step is displaceable from a first needle position to a second needle position when the plunger is moved from the first plunger position toward the second plunger position, the needle having a needle point extending from the housing when in the second needle position; and further wherein the positioning step includes placing the distal end of the housing against the injection site.

23. The method of claim 19, wherein the interlocking assembly of the syringe provided by the providing step is coupled with the plunger so as to be switched from the first condition to the second condition when the plunger is moved to the second plunger position; and further wherein the switching step is performed by moving the plunger to the second plunger position.

24. The method of claim 19, wherein movement of the shroud toward the extended position provides an indication to a patient that beneficial agent has been injected.

\* \* \* \* \*